(12) United States Patent
Fishbaine

(10) Patent No.: US 7,027,639 B2
(45) Date of Patent: Apr. 11, 2006

(54) HIGH SPEED OPTICAL IMAGE ACQUISITION SYSTEM WITH EXTENDED DYNAMIC RANGE

(75) Inventor: David Fishbaine, Minnetonka, MN (US)

(73) Assignee: CyberOptics Corporation, Golden Valley, MN (US)

( * ) Notice: Subject to any disclaimer, the term of this patent is extended or adjusted under 35 U.S.C. 154(b) by 0 days.

(21) Appl. No.: 10/217,910

(22) Filed: Aug. 13, 2002

(65) Prior Publication Data

US 2002/0191834 A1 Dec. 19, 2002

Related U.S. Application Data

(63) Continuation-in-part of application No. 09/522,519, filed on Mar. 10, 2000, now Pat. No. 6,549,647.
(60) Provisional application No. 60/175,049, filed on Jan. 7, 2000.

(51) Int. Cl.
G06K 9/00 (2006.01)

(52) U.S. Cl. ...................... 382/150; 382/147; 382/286; 348/132

(58) Field of Classification Search ................ 382/147, 382/151, 286, 150, 154, 145, 149, 166, 141, 382/291, 144; 348/132, 92, 126, 87, 154, 348/208.4, 208.16, 131; 250/559.34, 341.8, 250/341.7, 559.4, 559.46; 356/237.2, 243.1, 356/237.4, 239.1, 394, 615, 612, 603, 401, 356/614

See application file for complete search history.

(56) References Cited

U.S. PATENT DOCUMENTS 2,625,856 A 1/1953 Muller
3,777,061 A 12/1973 Takemura ............... 178/5.4 R
3,995,107 A 11/1976 Woywood ................ 178/7.1

(Continued)

FOREIGN PATENT DOCUMENTS

| DE | 40 11 407 A1 | 10/1991 |
|----|----|----|
| DE | 19 511 160 A1 | 3/1995 |
| EP | 0 453 977 A2 | 10/1991 |
| EP | 0660 078 A1 | 12/1994 |
| WO | WO 98/59490 | 6/1998 |
| WO | WO 99/12001 | 3/1999 |
| WO | WO 99/24786 | 5/1999 |
| WO | WO 0106210 A1 | 1/2001 |
| WO | WO 0154068 A2 | 7/2001 |
| WO | WO 02/01209 A1 | 1/2002 |
| WO | WO 02/01210 A1 | 1/2002 |

OTHER PUBLICATIONS

U.S. Appl. No. 09/522,519, filed Mar. 10, 2000, Skunes et al.
U.S. Appl. No. 09/524,133, filed Mar. 10, 2000, Fishbaine et al.

(Continued)

*Primary Examiner*—Bhavesh M. Mehta
*Assistant Examiner*—Sheela Chawan
(74) *Attorney, Agent, or Firm*—Westman, Champlin & Kelly, P.A.

(57) ABSTRACT

A high-speed image acquisition system includes a source of light; a sensor for acquiring a plurality of images of the target; a system for determining relative movement between the source and the target; and an image processor for processing the acquired images to generate inspection information relative to the target. The system has an extended dynamic range provided by controlling illumination such that the plurality of images is acquired at two or more different illumination levels. In some embodiments, the high-speed image acquisition system is used to perform three dimensional phase profilometry inspection.

25 Claims, 4 Drawing Sheets

U.S. PATENT DOCUMENTS

| | | | | |
|---|---|---|---|---|
| 4,270,863 A | * | 6/1981 | Trogdon | 356/71 |
| 4,541,010 A | | 9/1985 | Alston | 358/44 |
| 4,598,321 A | | 7/1986 | Elabd et al. | 358/213 |
| 4,641,972 A | | 2/1987 | Halioua et al. | 356/376 |
| 4,643,565 A | | 2/1987 | Goto | 356/24 |
| 4,677,473 A | | 6/1987 | Okamoto et al. | 358/101 |
| 4,782,394 A | | 11/1988 | Hieda et al. | 358/213.19 |
| 4,835,616 A | | 5/1989 | Morcom | 358/213.19 |
| 4,949,172 A | | 8/1990 | Hunt et al. | 358/101 |
| 4,963,024 A | | 10/1990 | Ulich | 356/342 |
| 4,984,893 A | | 1/1991 | Lange | 356/376 |
| 5,039,868 A | | 8/1991 | Kobayashi et al. | 250/572 |
| 5,069,548 A | | 12/1991 | Boehnlein | 356/376 |
| 5,091,963 A | | 2/1992 | Litt et al. | 382/8 |
| 5,103,105 A | | 4/1992 | Ikegaya et al. | 250/561 |
| 5,135,308 A | | 8/1992 | Kuchel | 356/376 |
| 5,278,634 A | | 1/1994 | Skunes et al. | 356/400 |
| 5,298,734 A | | 3/1994 | Kokubo | 250/208.1 |
| 5,307,152 A | | 4/1994 | Boehnlein et al. | 356/376 |
| 5,406,372 A | | 4/1995 | Vodanovic et al. | 356/394 |
| 5,424,552 A | | 6/1995 | Tsuji et al. | 250/548 |
| 5,450,204 A | | 9/1995 | Shigeyama et al. | 356/378 |
| 5,450,228 A | | 9/1995 | Boardman et al. | 359/209 |
| 5,455,870 A | | 10/1995 | Sepai et al. | 382/147 |
| 5,504,596 A | * | 4/1996 | Goto et al. | 359/24 |
| 5,546,127 A | | 8/1996 | Yamashita et al. | 348/297 |
| 5,555,090 A | | 9/1996 | Schmutz | 356/381 |
| 5,576,829 A | * | 11/1996 | Shiraishi et al. | 356/521 |
| 5,636,025 A | | 6/1997 | Bieman et al. | 356/374 |
| 5,646,733 A | * | 7/1997 | Bieman | 356/604 |
| 5,668,665 A | | 9/1997 | Choate | 359/663 |
| 5,684,530 A | | 11/1997 | White | 348/131 |
| 5,686,994 A | | 11/1997 | Tokura | 356/39 |
| 5,691,784 A | | 11/1997 | Häusler et al. | 349/1 |
| 5,708,532 A | | 1/1998 | Wartmann | 359/663 |
| 5,761,337 A | | 6/1998 | Nishimura et al. | 382/150 |
| 5,774,221 A | | 6/1998 | Guerra | 356/376 |
| 5,815,275 A | | 9/1998 | Svetkoff et al. | 356/376 |
| 5,862,973 A | | 1/1999 | Wasserman | 228/105 |
| 5,867,604 A | | 2/1999 | Ben-Levy et al. | 382/254 |
| 5,878,152 A | | 3/1999 | Sussman | 382/106 |
| 5,912,984 A | | 6/1999 | Michael et al. | 382/149 |
| 5,917,927 A | * | 6/1999 | Satake et al. | 382/149 |
| 5,926,557 A | * | 7/1999 | King et al. | 382/149 |
| 5,953,448 A | | 9/1999 | Liang | 382/154 |
| 5,969,819 A | | 10/1999 | Wang | 356/371 |
| 5,982,921 A | * | 11/1999 | Alumot et al. | 382/145 |
| 5,982,927 A | | 11/1999 | Koljonen | 382/168 |
| 5,991,461 A | | 11/1999 | Schmucker et al. | 382/284 |
| 5,995,232 A | | 11/1999 | Van Der Ven | 356/395 |
| 5,999,266 A | * | 12/1999 | Takahashi et al. | 356/613 |
| 6,028,673 A | | 2/2000 | Nagasaki et al. | 356/376 |
| 6,061,476 A | | 5/2000 | Nichani | 382/270 |
| 6,081,613 A | | 6/2000 | Ikurumi et al. | 382/147 |
| 6,084,712 A | | 7/2000 | Harding | 359/618 |
| 6,118,524 A | * | 9/2000 | King et al. | 356/237.1 |
| 6,180,935 B1 | | 1/2001 | Hoagland | 250/208.1 |
| 6,201,892 B1 | * | 3/2001 | Ludlow et al. | 382/149 |
| 6,232,724 B1 | | 5/2001 | Onimoto et al. | 315/161 |
| 6,268,923 B1 | | 7/2001 | Michniewicz et al. | 356/512 |
| 6,269,197 B1 | | 7/2001 | Wallack | 382/285 |
| 6,303,916 B1 | * | 10/2001 | Gladnick | 250/205 |
| 6,307,210 B1 | | 10/2001 | Suzuki et al. | 250/559.08 |
| 6,445,813 B1 | | 9/2002 | Ikurumi et al. | 382/147 |
| 6,496,254 B1 | | 12/2002 | Bostrom et al. | 356/237.2 |
| 6,522,777 B1 | * | 2/2003 | Paulsen et al. | 382/154 |
| 6,603,103 B1 | * | 8/2003 | Ulrich et al. | 250/205 |

OTHER PUBLICATIONS

U.S. Appl. No. 09/754,991, filed Jan. 5, 2001, Kranz et al.

Copy of International Search Report from Application No. PCT/US00/42760 with international filing date of Dec. 12, 2000.

Copy of International Search Report from Application No. PCT/US00/42764 with international filing date of Dec. 12, 2000.

Copy of International Search Report from Application No. PCT/US01/00330 with international filing date of May 1, 2001.

"Cognex and Sony Team Develops Machine–Vision Camera", *Vision Systems Design*, p. 15 (Feb. 1999).

"3–D Profilometry Based on Modulation Measurement", by Likun et al., vol. 19, No. 9, pp.1–11 (Sep. 1999).

"High Frame Rate Cameras", *Princeton Instruments Catalog of High Performance Digital CCD Cameras*, 2 pages (Oct. 1994).

"Area Array CCD Image Sensor 1024×1024 Pixels with Antiblooming", CCD Products, Thomson–CSF Semiconducteurs Specifiques, pp. 267–273 (1996).

"Accurate Machine Vision is the 'Telecentric Advantage'", 3 pages from website.

"Rank Order Morphological Hit–Miss Transform and Its Optical Implementation", by Huiquan et al., Acta Optica Sinica, vol. 19, No. 9, pp. 1256–1263 (Sep. 1999). Translation provided.

* cited by examiner

HIGH SPEED OPTICAL IMAGE ACQUISITION SYSTEM WITH EXTENDED DYNAMIC RANGE

CROSS REFERENCE TO CO-PENDING APPLICATION

This application is a Continuation-in-Part application of U.S. patent application Ser. No. 09/522,519, filed Mar. 10, 2000 now U.S. Pat No. 6,549,647, and entitled "Inspection System with Vibration Resistant Video Capture," which claims priority benefits from U.S. Provisional patent application Ser. No. 60/175,049, filed Jan. 7, 2000 and entitled "Improved Inspection Machine."

COPYRIGHT RESERVATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to the acquisition and subsequent construction of an extended dynamic range image using a high-speed imaging system.

BACKGROUND OF THE INVENTION

High-speed optical image acquisition systems are used in a variety of environments to analyze the physical characteristics of one or more targets. Generally, such systems include an image acquisition system, such as a camera, that can acquire one or more images of the target. The images are then analyzed to assess the target. In many cases, the inspection is performed while there is relative motion between the target and the image acquisition system. As used herein, a "high-speed" optical image acquisition system is any system that acquires images of one or more targets while there is relative motion between the target and an image acquisition system. One particular example of such a system includes a phase profilometry inspection system such as that used in some modern solder paste inspection systems.

Phase profilometry inspection systems are currently used to inspect three-dimensional aspects of target surfaces. The concept of phase profilometry is relatively simple. A pattern or series of patterns of structured light are projected upon a target at an angle relative to the direction of an observer. This can be likened to sunlight passing through a Venetian blind and falling upon a three-dimensional object, where the object is viewed from an angle that differs from that of the sunlight. The pattern is distorted as a function of the object's shape. Knowledge of the system geometry and analysis of the distorted image or images can provide a map of the object in three dimensions.

Generally, phase profilometry systems employ a source of structured, patterned light, optics for directing the structured, patterned light onto a three-dimensional object and a sensor for sensing an image of that light as it is scattered, reflected or otherwise modified by its interaction with the three-dimensional object.

Phase profilometry inspection can be performed while there is relative motion between the target and the inspection system. This feature is highly beneficial for automated inspection machines where throughput is very important. One example of a phase profilometry inspection system is the Model SE 300 Solder Paste Inspection System available from CyberOptics Corporation of Golden Valley, Minn. This system uses phase profilometry to measure height profiles of solder paste deposited upon a circuit board prior to component placement. The SE 300 System is able to acquire the images that it uses for three-dimensional phase profilometry while allowing continuous relative motion between the sensor and the target. This is because a strobe illuminator is operated to provide short exposure times thus essentially freezing motion. Specifics of the illumination and image acquisition are set forth in greater detail in the parent application.

Solder paste, itself, presents a relatively favorable target in that it is comprised of a number of tiny solder spheres. Because there are so many small, spherical reflectors in each solder deposit, in the aggregate, each solder deposit provides a substantially diffuse optical surface that can be illuminated and imaged by a sensor configured to receive diffusely scattered light. The relatively uniform reflectivity of the solder paste deposits facilitates imaging.

High-speed inspection systems such as the surface phase profilometry inspection described above provide highly useful inspection functions without sacrificing system throughput. Theoretically, such inspection systems would be highly useful for any inspection operation that requires height information as well as two-dimensional information from a system without adversely affecting system throughput. However, there are real-world hurdles that hinder the ability to extend the advantages of high-speed inspection beyond targets having relatively diffuse reflectivity such as solder paste.

Surfaces such as the underside of a ball grid array (BGA) or chip scale packages (CSP's) are difficult to inspect using current optical phase profilometry systems. Specifically, the balls on a BGA are constructed from reheated solder, rendering them substantially hemispherical and shiny. Illuminating the hemispherical shiny balls with a structured or directional light source will generate a bright glint from a portion of the surface near the specular angle. Conversely, there will be nearly no light returned by diffuse scattering from the remainder of the hemispherical surface. Imaging the ball with a sensor that is not configured to deal with this wide dynamic range of returned light levels would result in erroneous data.

When light falls upon any surface, some light will be specularly reflected and some will be diffusely scattered. Some surfaces (like a mirror) are predominantly specular in their reflections, and some surfaces (like a piece of paper) predominantly scatter light. Imaging any such surface, even highly specular surfaces, may be possible by extending the dynamic range of a sensor configured to receive diffusely scattered light. One way in which dynamic range has been extended in the past is by taking or acquiring multiple images of a target with different illumination levels and processing the images to discard image data such as saturated pixels or dark pixels. However, all dynamic range extension techniques currently known are believed to be applied solely to systems in which the target and inspection system do not move relative to each other while the multiple images are acquired. Thus, as defined herein, such systems are not "high-speed." In inspection systems where throughput cannot be sacrificed by pausing relative movement between the inspection system and the target, dynamic range extension itself is not easy to implement.

SUMMARY OF THE INVENTION

A high-speed image acquisition system includes a source of light; a sensor for acquiring a plurality of images of the target; a system for determining relative movement between the source and the target; and an image processor for processing the acquired images to generate inspection information relative to the target. The system has an extended dynamic range provided by controlling illumination such that a plurality of images is acquired at two or more different illumination levels. In some embodiments, the high-speed image acquisition system is used to perform three dimensional phase profilometry inspection.

DETAILED DESCRIPTION

Embodiments of the invention are applicable to any high-speed optical image acquisition system. While much of the disclosure is directed to inspection systems, particularly phase profilometry inspection systems, embodiments of the invention can be practiced in any image acquisition system where image acquisition occurs without pausing relative motion between a target and image acquisition system.

In the phase profilometry embodiments, the number of images in each image set is preferably equal to the number of relevant unknowns in the target. For example, if the target has three substantial unknowns, which might include height, reflectivity and fringe contrast, then three images of three differing projected patterns or phases of a single pattern or a suitable mix would be preferred. Thus, for embodiments with more than three unknowns, more images would be preferred, and vice versa.

Figure 1:
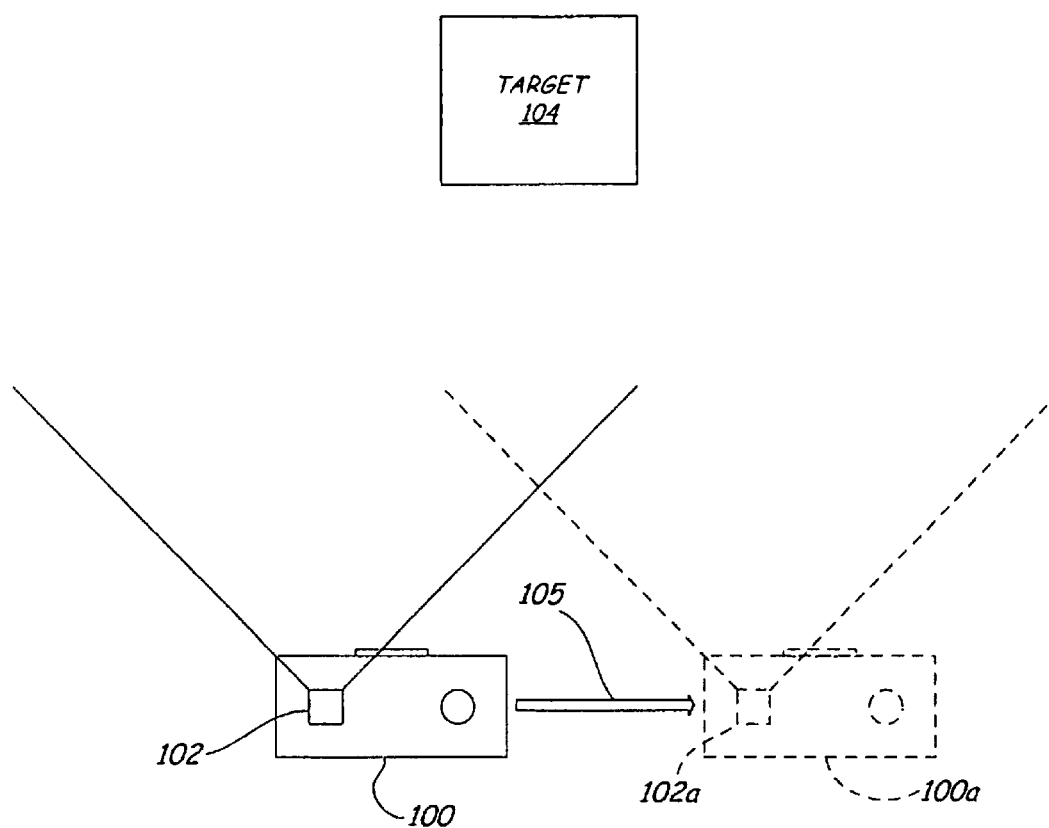
FIG. 1 is a diagrammatic view illustrating operation of a high-speed image acquisition system in accordance with an embodiment of the present invention.

FIG. 1 is a diagrammatic view illustrating operation of a high-speed image acquisition system in accordance with an embodiment of the present invention. A representative sensor 100 of a high-speed image acquisition system is shown with light source 102. Source 102 is flashed, or otherwise energized for a very short duration one or more times, during relative movement between sensor 100 and target 104 as indicated by arrow 105. One or more images of target 104 is/are acquired by sensor 100, corresponding to the flash(es), without pausing the relative motion. After a short interval, inspection system 100 has moved to a new location indicated at 100a in phantom. At the new location, while moving relative to target 104, illumination source 102a is flashed again, one or more times at an intensity that is different than the first flash or set of flashes. The relative flash intensities of the first and second sets of flashes are preferably measured, as will be described later in the specification. Sensor 100 acquires image(s) of target 104 corresponding to the subsequent set of flashes. Sensor 100 measures, or otherwise determines, the relative sensor movement between the first and second flashes, or sets of flashes and uses that information to register or cosite the two acquired image sets. In embodiments where the number of images in each set is one, the detector array used in sensor 100 is preferably an interline transfer CCD array or CMOS array.

Once the image sets are registered, a composite image with extended dynamic range can be created. Extended dynamic range is provided because if one image set has saturated or black portions, data from the other image can be used and normalized based on the measured illumination intensities or the measured ratio between the two intensities.

Target 104 may be a two-dimensional or three-dimensional object. Further, the illumination generated during either or both flashes can be of any suitable wavelength, including that of the visible spectrum.

Figure 2:
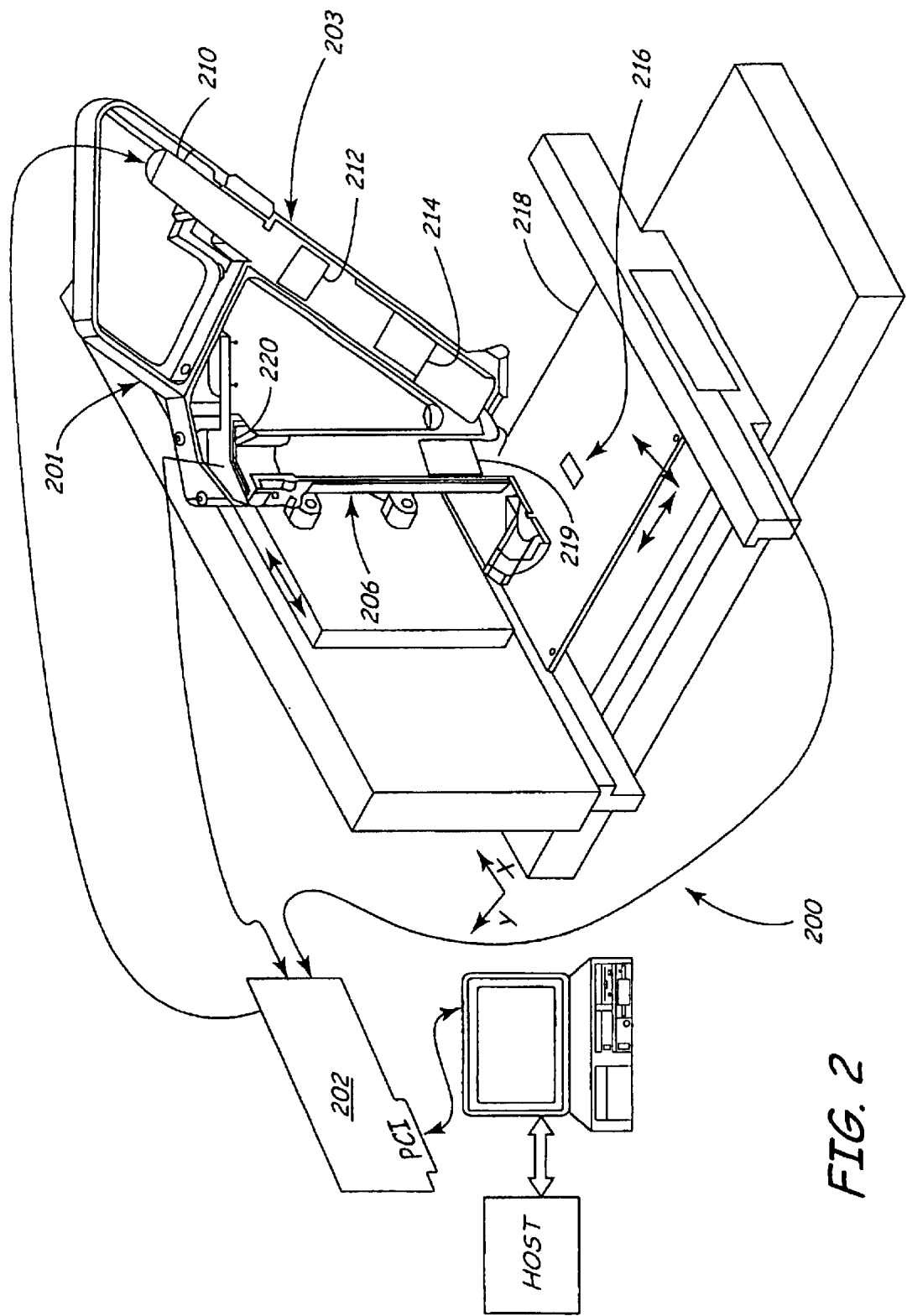
FIG. 2 is a diagrammatic view of an inspection system in which embodiments of the invention are particularly useful.

FIG. 2 is a diagrammatic view of an exemplary inspection system 200 in which embodiments of the present invention are useful. System 200 includes image processor 202 and sensor 201. Sensor 201 includes projector 203, and imager 206. Projector 203 includes illuminator 210, grating 212, and optics 214. Illuminator 210 is preferably a gas discharge flashlamp, such as a high intensity xenon arc lamp, but can be any light source capable of providing short duration light pulses, such as a pulsed laser or LED. Grating 212 imparts a pattern on the light passing therethrough, and optics 214 focuses the patterned light upon target 216 on circuit board 218. Imager 206 includes optics 219, which focus the image of target 216 upon array 220, which is preferably a frame transfer CCD array because each set of images includes more than one image in this embodiment. As the target moves in the Y direction relative to sensor 201, the relative position of the target is observed by processor 202 via position encoders (not shown). Processor 202 is coupled to projector 203 such that processor 202 triggers projector 203 to project a patterned image upon target 216 on circuit board 218 according to the observed position. Target 216 may be, for example, a solder paste deposit, an electrical component or a package of an electrical component. As motion continues in the Y direction, two more images are acquired to complete the set of three images used in this embodiment. The target motion relative to sensor 201 provides the phase shift required to generate the p, p+120 and p+240 degree images used in this embodiment to form a three-dimensional image of the target.

CCD array 220 provides data representative of the acquired images to image processor 202 which computes a height map of target 216 based upon the acquired images. The height map is useful for a number of inspection criteria.

Figure 3:
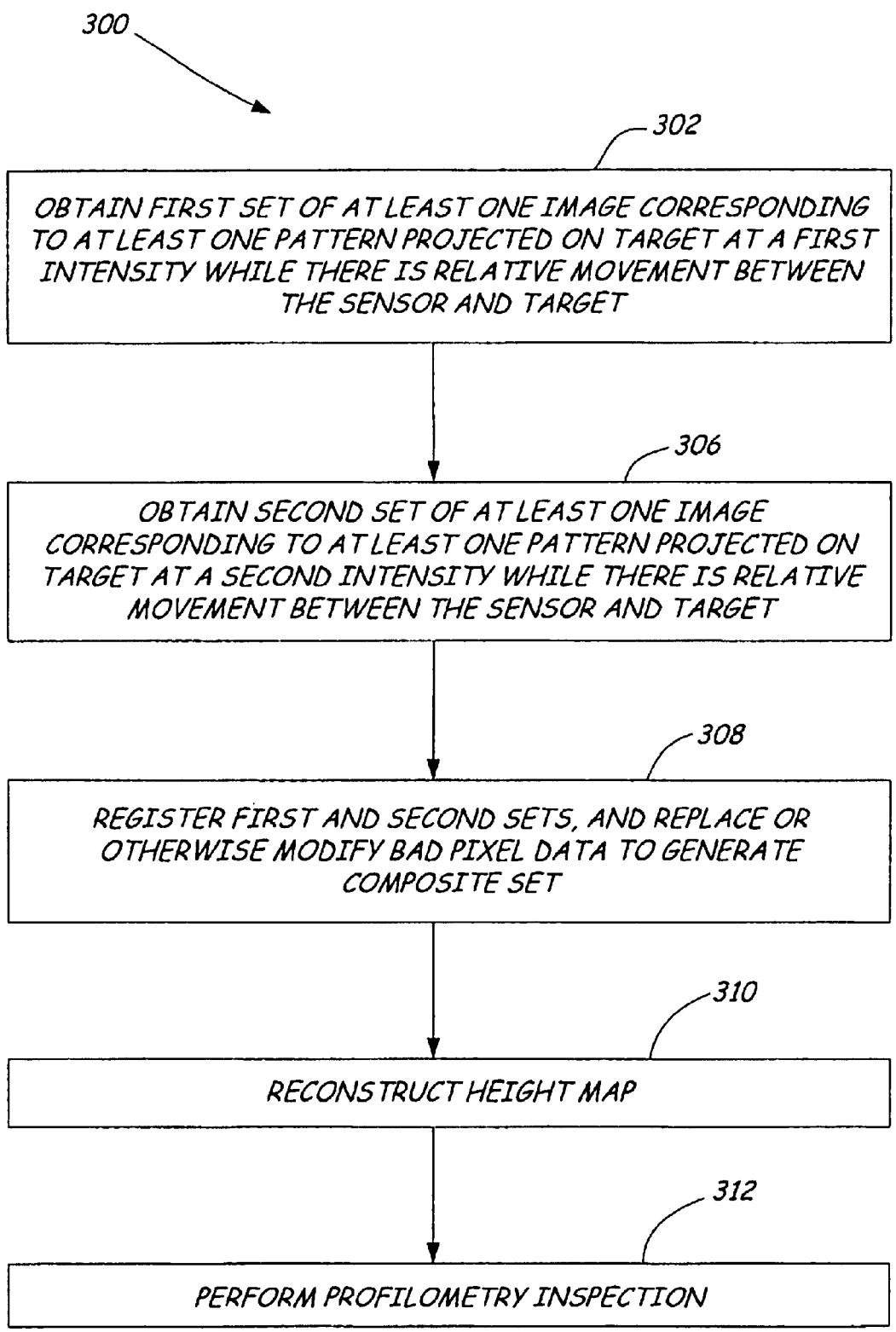
FIG. 3 is a flow diagram of a method of performing phase profilometry inspection in accordance with an embodiment of the present invention.

FIG. 3 is a flow diagram of an embodiment of the invention where extended dynamic range phase profilometry is performed using a high-speed inspection system. Method 300 begins at block 302, where a first set of at least one image is acquired while the acquisition system is moved relative to the target, and while the light source is flashed at a first illumination level. The first set of preferably three images is acquired in an extremely small amount of time in order to increase vibration immunity. For example, the first triplet can be obtained in 1 millisecond or less, as disclosed in the parent application. Each image of the first set is acquired while a different phase or pattern is projected onto the target. Preferably, a sinusoidal fringe pattern is used, and each image is separated from the other by a lateral distance that corresponds to approximately 120 degrees of phase change. For example, the images can be acquired at p, p+120, and p+240 degrees, where p is some arbitrary phase.

Typically, throughout inspection, there is continuous relative motion between sensor 201 and target 216. At block 306, a second set of at least one image is obtained while target 216 is illuminated at a second illumination level that differs from the first illumination level. Preferably, the second set consists of three images obtained with differing phases of a sinusoidal fringe pattern. The second set is also obtained within an interval of preferably one millisecond, but need not be within any specific period from the acquisition of the first set, as long as the difference is not so great that the two sets cannot be related to one another. Preferably, however, if the first set of images is acquired at p, p+120, and p+240 degrees, the second set is acquired at p+360n, p+360n+120 and p+360n+240 degrees, where n is an integer. In this manner, the images of the fringe pattern on target 216 will be identical except for differences due to the intentional illumination level change and the relative motion between sensor 201 and target 216 corresponding to 360n degrees.

At block 308, the first and second sets of at least one image are registered. This can be performed by adjusting one or both sets of images based upon measured, or otherwise known movement that occurred between acquisition of the first and second sets. Additionally, in some embodiments, it is possible to apply image processing techniques to the sets of images themselves to recognize patterns or references in the images and manipulate the images such that the references are aligned. Further still, measured motion between the first and second sets of acquisitions can be used to perform a first stage manipulation where one or both sets are manipulated for a coarse alignment. Then, the results of the coarse alignment are processed to identify patterns or references in the coarse-aligned images in order to finely adjust the images. Once the images are registered, the dynamic range can be extended as discussed above.

Generally, the brighter set of images (those obtained using the greater of the illumination levels) should be usable until saturation, presuming only that the detector and analog circuitry are linear, or at least stable (in which case non-linearity can be calibrated out). However, any suitable technique or algorithm can be used.

Some embodiments of the present invention require that the difference in illumination levels be precisely controlled. Although it may be technically possible to provide an illumination circuit with a precisely-controlled intensity, it is preferred that the illumination levels be only approximately controlled, but then measured to the required precision during use. As an example, the brighter illumination level may be one hundred times brighter than the dimmer level. In one embodiment, illumination levels are measured during use and used to correct for variations from one set to the next with sufficient precision. Preferably, the required precision is approximately equal to the smallest relative error detectable by the analog to digital converter. Thus, with a 10-bit converter, it would be sufficient to measure the relative light levels to a precision of one part in $2^{10}$; with a ratio of light levels of 100 to 1, the resulting dynamic range would be 100 times $2^{10}$ or about 100,000 to 1.

This approach is preferred due to the difficulty of controlling the strobe discharge with the required precision.

Alternatively, each set of images can be constructed into height maps before dynamic range extension and then three dimensional pixels (zetels) from the bright map can be replaced with zetels from the dim map depending on whether there was saturation in the images used to construct the bright map. The strobe intensities must still be well controlled or measured, since such intensity errors affect the height reconstruction, but the task is easier since only the nominally-equal strobe intensities within the set used to construct each height map need be measured or controlled; the magnitude of the large ratio between sets need not be known or controlled accurately.

Other normalization techniques are also possible. For instance, each image in the set can be normalized (that is, divided) by its corresponding measured strobe intensity. Then the normalized pixels can be freely chosen from one set or the other, based on their positions in their respective dynamic ranges, with the height reconstruction done later on the composite image set thus produced. This technique relies on the fact that phase reconstruction is not affected by a scaling that is applied uniformly to all the phase images. The suitability of a particular technique may depend on the details of the hardware or software used to make the selection.

At block 310, a height map is reconstructed using the composite set of image data from step 308. The manner in which the height map is generated can include any of the well-known phase profilometry height reconstruction techniques. Once the height map is reconstructed, step 312 is executed where profilometry inspection is performed on the reconstructed height map. This inspection can include extracting summary measures such as height, volume, area, registration, coplanarity, maximum height range, surface contours, surface roughness . . . etc.

Figure 4:
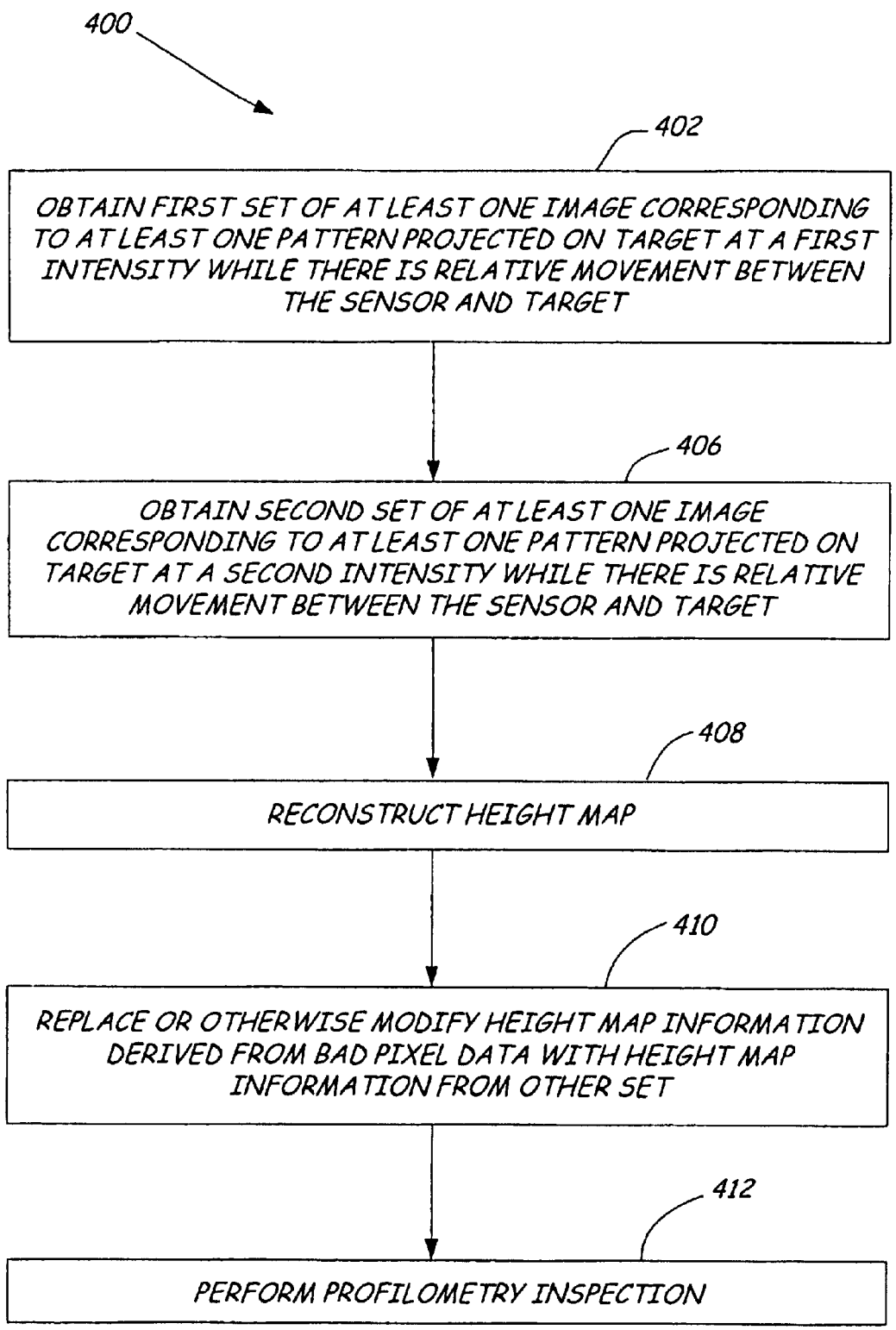
FIG. 4 is a flow diagram of another method of performing phase profilometry inspection in accordance with another embodiment of the present invention.

FIG. 4 is a flow diagram of another method of performing phase profilometry inspection in accordance with another embodiment of the present invention. Method 400 begins similarly to method 300, with steps 402, and 406 providing for the acquisition of first and second sets of images while the image acquisition system moves relative to a target surface. However, method 400 differs from method 300 in one important respect. Specifically, after step 406, method 400 provides step 408 where height maps, one for each set of acquired images, are reconstructed. Then, at step 410, the height maps are reviewed to determine if they include portions that were based on bad pixel data, such as saturated pixels. If a first height map includes such a portion, a corresponding portion of the second height map is reviewed to determine if its pixel data for that portion is usable. If so, the portion of the first height map is replaced with the corresponding portion of the second height map. Since the maps are generated prior to step 410, the replacement operation need not take into account the difference in illumination intensity between the images used for the first height map and that of the second height map as long as the variation of illumination intensity within a given set is the same, or can be measured and corrected. At step 412, the final height map is used in profilometry inspection. Although FIG. 4 illustrates acquiring the second set before performing any height construction, it is also possible to reconstruct the first height map before acquiring the second set of images.

Although the present invention has been described with reference to preferred embodiments, workers skilled in the art will recognize that changes may be made in form and detail without departing from the spirit and scope of the invention.

What is claimed is:

1. A high-speed image acquisition system comprising:
a sensor movable relative to a target;
an illuminator adapted to direct illumination upon the target at a plurality of illumination levels;
wherein the sensor obtains a first set of at least one image at a first illumination level during relative motion between the sensor and the target, and the sensor obtains a second set of at least one image at a second illumination level of the plurality of illumination levels during relative motion between the sensor and the target;

wherein the first and second illumination levels differ from each other by a known ratio, and wherein an unusable portion from one set of at least one image is replaced based upon the other set of at least one image and the known ratio; and an image processor coupled to the sensor and adapted to create an extended dynamic range image based at least in part upon cositing the first set of at least one image with the second set of at least one image.

2. The system of claim 1, wherein the illuminator is a stroboscopic illuminator.

3. The system of claim 2, wherein the illuminator is a gas discharge strobe.

4. The system of claim 1, wherein the illuminator is movable relative to the target.

5. The system of claim 1, and further comprising a position measurement system coupled to the sensor, the position measurement system providing an indication to the image processor relative to displacement occurring between acquisition of the first and second sets.

6. The system of claim 5, wherein the image processor registers the first and second sets based upon the indication.

7. The system of claim 6, wherein the image processor registers the first and second sets based upon image processing of the first and second sets.

8. The system of claim 1, wherein the target is an electrical component.

9. The system of claim 1, wherein the target is a package of an electrical component.

10. A high-speed inspection system comprising:

a single source disposed to project light upon a target at a plurality of illumination levels;

an imaging system for acquiring a plurality of sets of at least one image, wherein a first set is related to a first illumination level of the plurality of illumination levels, and a second set is related to a second illumination level of the plurality of illumination levels, during relative movement between the imaging system and the target;

a processor for processing the acquired images to generate inspection information with an extended dynamic range; and wherein the source is adapted to project patterned illumination, wherein the pattern is a sinusoidal fringe pattern, and wherein the first set of at least one image includes three images acquired at phases that are substantially P, P+120, and P+240 degrees of the sinusoidal function.

11. The system of claim 10, wherein the first set is acquired within one millisecond.

12. The system of claim 10, wherein the second set of at least one image includes three images acquired at phases that are substantially p+360n, p+360n+120, and p+360n+240 degrees of the sinusoidal function, where n is an integer.

13. The system of claim 12, wherein the second set is acquired within one millisecond.

14. The system of claim 10, wherein the source is a strobe.

15. The system of claim 14, wherein the source includes a gas discharge flashlamp.

16. The system of claim 15, wherein the source is a xenon arc flashlamp.

17. The system of claim 10, wherein the first and second sets of images are registered using image processing techniques.

18. The system of claim 10, and further comprising a system for measuring displacement between the imaging system and the target during the interval between acquisition of the first and second sets, and wherein the first and second sets are registered based at least in part upon the measured displacement.

19. The system of claim 10, and further comprising an illumination sensor for sensing the first and second illumination levels to provide a ratio therebetween.

20. The system of claim 19, wherein the processor registers the first and second sets to create a composite set.

21. The system of claim 19, wherein portions of images in one set are replaced by portions of images in the other set by normalizing the portions in the other set using the ratio.

22. The system of claim 10, and further comprising an illumination sensor for sensing the first and second illumination levels to provide a difference therebetween.

23. The system of claim 22, wherein the processor registers the first and second sets to create a composite set.

24. The system of claim 22, wherein portions of images in one set are replaced by portions of images in the other set by normalizing the portions in the other set using the ratio.

25. A method of inspecting a target with a high-speed inspection system, the method comprising:

obtaining a first image of the target at a first illumination level with a sensor while the sensor and target move relative to each other;

obtaining a second image of the target at a second illumination level with the sensor while the sensor and target move relative to each other, wherein the first and second illumination levels differ from each other by a known amount;

replacing an unusable portion of one of the first and second images with a corresponding portion of the other of the first and second images by normalizing the corresponding portion based upon the known amount of difference in illumination levels, to create a composite image; and processing the composite image to generate inspection information relative to the target.

* * * * *